United States Patent [19]

Vincent et al.

[11] 4,246,267

[45] Jan. 20, 1981

[54] AMINOPIPERIDINES, THEIR PRODUCTION AND THE PHARMACEUTICAL COMPOSITIONS INCORPORATING THEM

[75] Inventors: Michel Vincent, Bagneux; Georges Remond, Versailles; Michel Laubie, Vaucresson, all of France

[73] Assignee: Science Union et Cie, Suresnes, France

[21] Appl. No.: 948,536

[22] Filed: Oct. 4, 1978

Related U.S. Application Data

[63] Continuation-in-part of Ser. No. 789,564, Apr. 21, 1977, abandoned.

[30] Foreign Application Priority Data

Apr. 29, 1976 [FR] France ................................ 76 12671

[51] Int. Cl.³ .................. A61K 31/445; C07D 211/58

[52] U.S. Cl. ................................... 424/267; 546/224; 546/197

[58] Field of Search ........................ 424/267; 546/224

[56] References Cited

U.S. PATENT DOCUMENTS

| 2,846,437 | 8/1958 | Elpern .................................. 546/224 |
| 3,371,094 | 2/1968 | Zenitz .................................. 546/224 |
| 3,869,463 | 3/1975 | Archibald ........................... 546/224 |

*Primary Examiner*—Norma S. Milestone
*Attorney, Agent, or Firm*—Gordon W. Hueschen

[57] ABSTRACT

This invention relates to 4-aminopiperidines and more precisely to 4-aminopiperidines the nitrogen atom of the piperidine ring is substituted with an aryl lower alkyl side-chain.

This invention also relates to processes for producing the same.

This invention further extends to pharmaceutical compositions and to the method of using the same.

25 Claims, No Drawings

AMINOPIPERIDINES, THEIR PRODUCTION AND THE PHARMACEUTICAL COMPOSITIONS INCORPORATING THEM

This is a continuation-in-part of U.S. application Ser. No. 789,564, filed Apr. 21, 1977, now abandoned.

DESCRIPTION OF THE PRIOR ART

The prior art may be illustrated by the French drug patents 2429M, 2430M and 2431M J. L. Archibald J. Med. Chem. 17 736 and 739 (1974).

SUMMARY OF THE INVENTION

This invention relates to 4-aminopiperidines. The nitrogen atom of the piperidine ring is substituted with an aryl lower alkyl side-chain. More precisely this invention provides new 1-aryl alkylene 4-aminopiperidines of the formula I

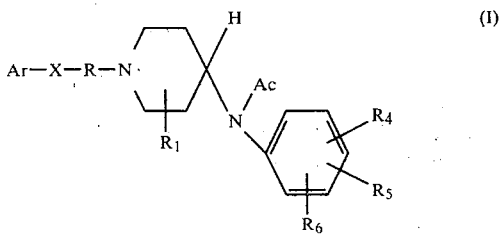

in which
$R_1$ is a hydrogen or a lower alkyl radical;
R is an alkylene chain having from 2 to 4 carbon atoms which may be substituted with one or more lower alkyl radicals;
X is a sulphur atom or a grouping

in which $R_2$ is a hydrogen, a lower alkyl carbonyl residue, a lower alkenyl radical or a lower alkyl radical;
Ac is an acyl residue from an alkyl carboxylic acid having up to 10 carbon atoms;
$R_4$, $R_5$ and $R_6$ which are the same or different represent a hydrogen, a halogen, a lower alkyl radical, a lower alkoxy or a lower alkylene dioxy;
and Ar is an aromatic ring, homo- or heterocyclic, selected from the group consisting of
(a) an unsubstituted or substituted phenyl radical of the general formula

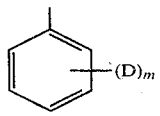

wherein D is a halogen, a lower alkyl radical, a lower alkenyl radical, a lower alkoxy, a lower alkenyloxy, a lower alkynyloxy, a lower alkylthio, a hydroxy carbonyl, a lower alkoxy carbonyl, a nitro group, an amino, a lower alkyl amino, a dilower alkyl amino, a lower alcylamino, a sulphonamido, a lower alkyl amino sulphonyl, a dilower alkyl amino sulphonyl, a lower alkyl sulphonyl, an amino carbonyl, a cyano, a trifluoromethyl or a lower alkylene dioxy, and m is O or an integer from 1 to 5,
(b) a bicyclic radical of the general formula

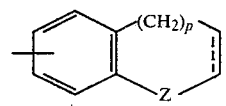

in which Z is an imino radical NH and p is an integer from 0 to 2
or Z is a sulphur atom and p is an integer from 1 to 3 and the dotted line means an optional double bond
and (c) a thienyl radical which may be substituted with a lower alkyl radical.

DESCRIPTION OF THE PREFERRED EMBODIMENTS

This invention relates to novel 4-amino piperidines and their production.

More particularly it relates to 4-amino piperidine the nitrogen of the piperidinyl ring being substituted with an aryl alkylene side-chain.

Specifically this invention provides as new compounds, the aryl alkylene piperidines of the general formula I

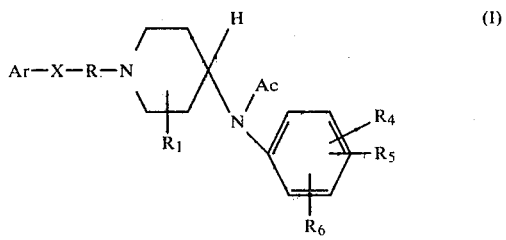

in which
$R_1$ is a hydrogen or a lower alkyl radical;
R is an alkylene chain having from 2 to 4 carbon atoms which may be substituted with one or more lower alkyl radicals;
X is a sulphur atom or a grouping

in which $R_2$ is a hydrogen, a lower alkyl carbonyl residue, a lower alkenyl radical or a lower alkyl radical;
Ac is an acyl residue from an alkyl carboxylic acid having up to 10 carbon atoms;
$R_4$, $R_5$ and $R_6$ which are the same or different represent a hydrogen, a halogen, a lower alkyl radical, a lower alkoxy or a lower alkylene dioxy;
and Ar is an aromatic ring, homo- or heterocyclic, selected from the group consisting of
(a) an unsubstituted or substituted phenyl radical of the general formula

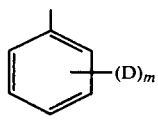

wherein D is a halogen, a lower alkyl radical, a lower alkenyl radical, a lower alkoxy, a lower alkenyloxy, a lower alkynyloxy, a lower alkylthio, a hydroxy carbonyl, a lower alkoxy carbonyl, a nitro group, an amino, a lower alkyl amino, a dilower alkyl amino, a lower acylamino, a sulphonamido, a lower alkyl amino sulphonyl, a dilower alkyl amino sulphonyl, a lower alkyl sulphonyl, an amino carbonyl, a cyano, a trifluoromethyl or a lower alkylene dioxy,
and m is O or an integer from 1 to 5;
(b) a bicyclic radical of the general formula

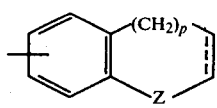

in which Z is an imino radical NH and p is an integer from 0 to 2,
or Z is a sulphur atom and p is an integer from 1 to 3 and the dotted line means an optional double bond;
and (c) a thienyl radical which may be substituted with a lower alkyl radical.

Among the compounds of general formula I it may be cited—the compounds having the general formula I′

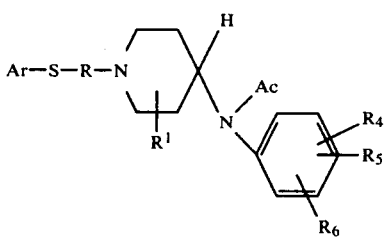
(I′)

in which the definitions of the substituents Ar, R, Ac, $R_1$, $R_4$, $R_5$ and $R_6$ remain unaltered, and namely the phenylthio alkylene piperidines having the formula $I_A$

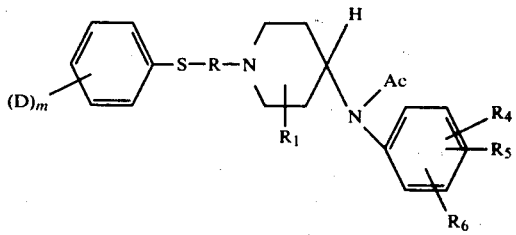
($I_A$)

in which the definitions of the substituent D, R, $R_1$, Ac, $R_4$, $R_5$, $R_6$ and m remain unaltered, the thienylthio alkylene piperidines of the formula $I_B$

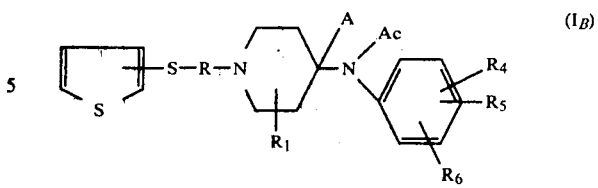
($I_B$)

in which the substituents R, $R_1$, Ac, $R_4$, $R_5$ and $R_6$ keep the above-given definitions
and the compounds having the general formula I″

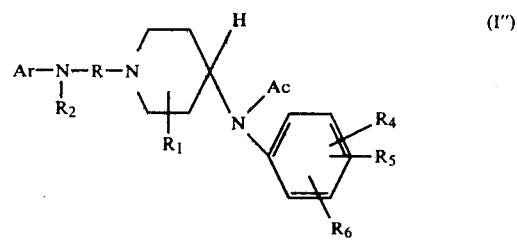
(I″)

in which the definitions of the substituents R, $R_1$, $R_2$, $R_4$, $R_5$, $R_6$ and Ac remain unaltered, and namely the compounds having the formule $I_C$

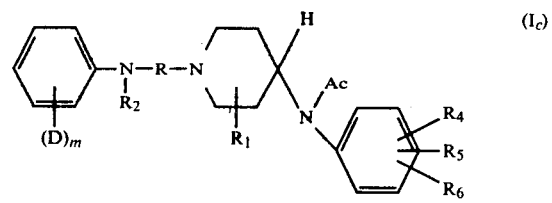
($I_c$)

in which the substituents D, R, $R_1$, $R_4$, $R_5$, $R_6$ et m are defined as above-indicated and $R_2$ is a hydrogen, a methyl, an ethyl, an allyl or an acetyl group The compounds of general formula I are of basic character and may be converted into a salt by adding a mineral or organic acid, preferably a therapeutically-compatible acid.

When $R_1$ is a lower alkyl or when R is a lower alkylene chain substituted with an alkyl radical there is at least an asymetric carbon atom and the compounds of resulting formula I may exist in the form of resolvable optically-active isomers or geometric diastereoisomers. The resolution step is performed for example, by salification with an optically-active organic acid such as a carboxylic acid, a sulphonic acid or a phosphoric acid.

As far as the invention is concerned the expression "lower alkyl" is intended to designate a saturated hydrocarbyl radical in straight or branched chain having from 1 to 6 carbon atoms. Such alkyl groups may be substituted with a hydroxy, a lower acyloxy, a lower alkoxy, or a dilower alkylamino.

Examples of such lower alkyl are the methyl radical, ethyl, n-propyl, isopropyl, n-butyl, sec-butyl, n-pentyl, neo-pentyl, sec-pentyl, tert-butyl, n-hexyl, sec-hexyl, acetoxyethyl, methoxymethyl, ethoxymethyl, ethoxyethyl, β-hydroxyethyl, the diethylamino ethyl radical, and the like.

The term "halogen" preferably designates a fluorine or a chlorine atom. It may also designate a bromine or iodine.

The term "lower alkenyl" designates an unsaturated hydrocarbon radical having one to three carbon-carbon double bonds, including from 2 to 10 carbon atoms in straight or branched chain such as allyl, methallyl, isopentenyl, dimethylallyl, butenyl, triallylmethyl and pentadienyl, and the like.

The term "lower alkynyl" means a hydrocarbon radical having a triple bond, of 2 to 6 carbon atoms, such as ethynyl, prop-2 ynyl, prop-1-ynyl, or 1-methyl but-2 ynyl, and the like.

The acyl residue is preferably that derived from a lower alkylcarboxylic acid, the alkyl chain of which may be substituted. Examples of suitable acyl residues are those arising from acetic acid, propionic acid, butyric acid, di-n-propylacetic acid, isovaleric acid, caproic acid, diethylamino acetic acid, pimelic acid, succinic acid, $\beta$-ethoxy $\beta$-ethoxy acetic acid.

When Ar is an unsubstituted or substituted phenyl radical (a) Ar can be, for example, unsubstituted phenyl, o-halophenyl, m-halophenyl, p-halophenyl, 2,4-dihalophenyl, 3,5-dihalophenyl, 2,4,6-trihalophenyl, tetrahalophenyl or pentahalophenyl, where halo denotes fluorine, chlorine, bromine or iodine, preferably fluorine or chlorine, o-, m- or p-tolyl, xylyl, 3- or 4-allylphenyl, 2-, 3- or 4-methoxyphenyl, 2,4,6-trimethoxyphenyl, 4-allyloxyphenyl, 3-ethynyloxyphenyl, 2-, 3- or 4-methylthiophenyl, 2-, 3- or 4-carboxyphenyl, 2-, 3- or 4-ethoxycarbonylphenyl, 3- or 4-nitrophenyl, 2-, 3- or 4-aminophenyl, 2-, 3- or 4-(N-methylamino)phenyl, 2-, 3- or 4-(N,N-diethylamino)phenyl, 4-acetamidophenyl, 4-methylsulphonamido, 3-sulphonamidophenyl, 4-(N-ethylamino)sulphonylphenyl, 3-(N,N-N,N-dimethylamino)sulphonylphenyl, 4-aminocarbonylphenyl, 3- or 4-cyanophenyl, 3- or 4-trifluoromethylphenyl, 3,4-methylenedioxyphenyl or 3,4-ethylenedioxyphenyl, and the like. When D is tert-butyl or other group which would cause steric hindrance, only one or two of such groups are on the phenyl ring and such groups, if more than one, would not be in the 2 and 6 positions of the phenyl ring.

When Ar is a bicyclic radical, it may be a indolinyl, a dihydroindolinyl radical, a benzothienyl radical, a dihydrobenzothienyl radical, a benzothiopyranyl radical, or a thiachromenyl radical.

When Ar is a substituted thienyl radical it may be a 3-methylthienyl-2 radical, a 4-methylthienyl-2 radical, a 5-ethylthienyl radical or a 2-isopropyl thienyl radical. When Ar is a thienyl radical, the thio group is preferably attached to the carbon 2 or to the carbon 3.

The compounds of general formula I which contains at least one asymetric carbon may be resolved into their optical isomers by salification with an organic optically-active acid. Examples of suitable optically-active acids are d-tartaric acid, 1-ketogulonic acid, ascorbic acid, 1-menthoxy acetic acid, abietic acid, NN-dimethyltartramic acid, d-camphosulphonic acid, d-glucose 1-phosphoric acid and d-glucose 1,6-phosphoric acid.

The compounds of general formula I may also be salified by adding a mineral or organic acid, preferably a therapeutically-compatible acid. However the acids which are not therapeutically-compatible may form salts which are useful for isolating, purifying or characterizing the resultant material.

Examples of useful acids are hydrochloric, hydrobromic, hydroiodic, sulphuric, nitric, phosphoric or sulphurous acids; formic, acetic, valeric, lauric, benzoic, naphtoic, pamoic acids; p.bromobenzene sulphonic, ethane sulphonic, isethionic, methanesulphonic acids; nicotinic, 5-methyl thiazol carboxylic, thienyl carboxylic, indolyl acetic acids; ethyl phosphoric acid.

The compounds of general formula I as well as the salts thereof are endowed with interesting pharmacological properties. They exert namely anti-hypertensive properties. In contrast to the strong neuroleptic and analgetic properties shown by the known 4-amino piperidines previously described in the BSM 2429, BSM 2430 and BSM 2431, they do not exert any analgetic effect and may be wholly differentiated thereof. They find a therapeutic use in human or veterinary medicine as a drug for hypertension without showing the risk of noxious side effect of central nervous origin.

Due to their powerful pharmacological properties, the following compounds are those which are presently preferred:

1-[2(-thienyl-2-thio)-ethyl]4-(N-phenyl-N-propionylamino) piperidine,

1-[2-(2,(-dimethyl phenylthio)-ethyl]-4-(N-phenyl-N-propionylamino) piperidine, 1-(phenylaminoethyl)-4-(N-phenyl-N-propionylamino) piperidine, 1-(N-phenyl-N-methylamino-ethyl)-4-(N-phenyl-N-propionylamino) piperidine, 1-[(2,6-dichlorophenyl) amino-ethyl]-4-(N-phenyl-N-propionylamino) piperidine, 1-[(N-phenyl-N-acetylamino)-ethyl]-4-(N-phenyl-N-propionylamino) piperidine, 1-[(2,6-dimethylphenyl) aminoethyl]-4-(N-phenyl-N-propionylamino) piperidine, 1-[(N-phenyl-N-allylamino)-ethyl]-4-(N-phenyl-N-propionylamino) piperidine, and the acid addition salts thereof.

In view of therapeutic use, the compounds of general formula I are administered in the form of pharmaceutical compositions in which the active ingredient is admixed with an inert non-toxic pharmaceutically-acceptable carrier.

Among the pharmaceutical compositions there may be more particularly cited those which are intended for the oral, parenteral, sublingual, or rectal routes.

They include, namely, the ampules, phials, multidosage flasks, tablets, coated tablets, dragées, soft gelatin capsules, granulates, drops, syrups, sublingual tablets and suppositories.

The pharmaceutical compositions according to the invention may be prepared by the processes known in pharmacotechnology. The used inert carriers are preferably water or saline solutions, previously sterilized for the injectible solutions or suspensions; talc, calcium carbonate, magnesium phosphate, magnesium stearate, formolated casein, and gelatine for the tablets or capsules; cocoa butter or polyethylene glycol stearates for the suppositories; sugar, syrup of arabic gum, glycerol or water for the liquid preparations.

The useful dosages may broadly vary depending on the age and the weight of the patient, and the severity of the disease to be treated. Practically it may range from 1 to 250 mg of a compound of general formula I or a salt thereof per unit dosage and from 2 to 1000 mg per day in the man.

This invention also extends to a process for preparing a compound of general formula I in which an 4-aminopiperidine of formula II

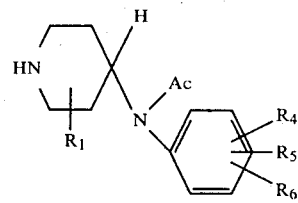

in which the substituents $R_1$, $R_4$, $R_5$, $R_6$ and Ac are defined as above-given, is reacted with an aryl alkyl ester of formula III $$Ar-X-R-Y \quad (III)$$

wherein Ar, X, and R are defined as previously given and Y is a halogen, or the acyl radical of a lower alkyl- or an aryl sulphonic acid to produce a compound of general formula I which may be, when desired, salified by adding a mineral or organic acid or resolved into its optically-active isomers or diastereoisomers by means of chemical or physical methods, or acylated by means of a carboxylic acid having from 1 to 10 carbon atoms or a functional derivative thereof when X is an imino group-NH—.

According to a preferred feature of this invention, the process is performed in an inert solvent in the presence or in the absence of a basic agent.

The inert solvent is preferably an aprotic polar solvent such as dimethyl formamide, dimethyl acetamide, dimethyl sulfoxide, hexamethyl phosphorotriamide or acetonitrile. It is also convenient to use a halogenated solvent such as methylene chloride or dichloroethane, either an aromatic hydrocarbon such as benzene, toluene, xylene or a cycloalkane such as cyclopenta or cyclohexane.

The esters of formula III are preferably those which derive from an acyl group which may easily be split such as methane sulphonic acid, ethane sulphonic acid, benzene sulphonic acid, p.toluene sulphonic acid, bromobenzene sulphonic acid and the like. When a bromide is used, it is more particularly convenient to perform the condensation in the presence of an alkali-metal iodide and in a dialkyl ketone as solvent, for example, acetone, methylisobutyl ketone, or methylethyl ketone.

As a basic agent it may be used a lower trialkylamine such as triethylamine, a dilower alkyl arylamine such as dimethylaniline or a pyridine base such as pyridine, collidine, lutidine or 4-dimethylaminopyridine.

The basic agent may also be an excess of the amino piperidine of formula II or the inert solvent itself when it is basic, for example dimethyl formamide or hexamethyl phosphorotriamide.

The invention also includes another process for producing the compounds oformula I which comprises condensing an arylalkyl ester of formula III $$Ar-X-R-Y \quad (III)$$

in which Ar, X, R and Y have the above-given meanings with a 4-aminopyridine of formula VI

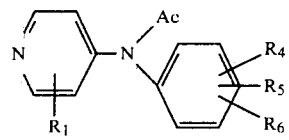

wherein the substituents $R_1$, Ac, $R_4$, $R_5$ and $R_6$ have the above-given meanings to produce a pyridinium salt of formula VII

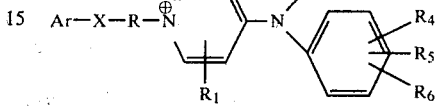

in which the substituents Ar, X, R, $R_1$, Ac, $R_4$, $R_5$ and $R_6$ have the above-given definitions which is further reduced by catalytic hydrogenation or by means of an alkali-metal complex hydride to obtain a compound of formula I.

According to this process the reduction step is carried out either by hydrogenation in the presence of palladium or platinum, by means of potassium or sodium borohydride or by means of lithium alumino hydride.

This invention further includes a process for producing the compounds of formula I which consists in condensing an aryl lower alkanol of formula VIII $$Ar-X-R-OH \quad (VIII)$$

in which Ar, X and R have the previously-given meanings with a 4-amino piperidine of formula II

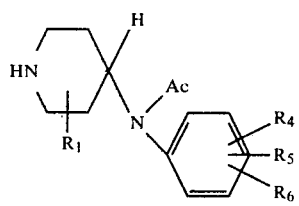

wherein $R_1$, $R_4$, $R_5$, $R_6$ and Ac have the previously given meanings in the presence of a hydrogenation catalyst to produce a compound of general formula I.

Preferably the hydrogenation catayst is Raney Nickel and more precisely Raney Nickel WR.

The compounds of Formula I may also be produced according to the process which consists in submitting an aryl lower alkyl piperidine of the formula V

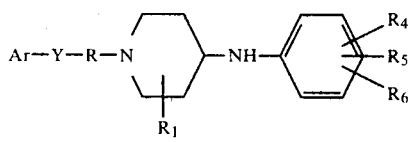

in which Ar, X, R, and $R_1$ have the above given definitions and $R_4$, $R_5$, and $R_6$, which are the same or different, represent hydrogen, halogen, lower alkyl, lower alkoxy or a lower alkylene dioxy radical, to the action of an acylating agent deriving from an alkyl carboxylic acid having from 1 to 10 carbon atoms and recovering the desired compound of formula I.

Usually the acylating agent is a halide of an alkyl carboxylic acid, for example, the acid chloride, or the alkyl carboxylic acid itself in the presence of a dehydrating agent such as a dilower alkyl, or a dicycloalkyl carbodiimide.

The compounds of formula V may conveniently be produced in condensing an aryl lower alkyl ester of formula III

     (III)

in which Ar, X, R and Y have the above-given definitions with a blocked piperidone of the formula XII

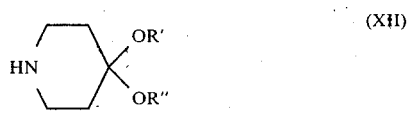     (XII)

wherein R' and R" the same or different are lower alkyl or together represent a lower alkylene chain having 2 or 3 carbon atoms to produce an aryl lower alkyl piperidine of the formula XIII

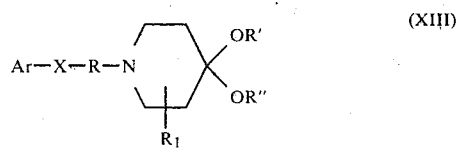     (XIII)

in which Ar, X, R, $R_1$, R' and R" are defined as above which is further hydrolyzed in acidic medium or submitted to a metathesis with a carbonylated derivative, for example, to produce the corresponding piperidone of the formula XIV

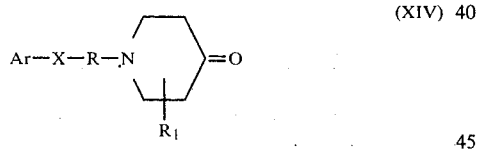     (XIV)

condensation of the latter with an arylamine of the formula XV

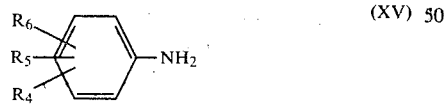     (XV)

wherein the substituents $R_4$, $R_5$ and $R_6$ have the previously-given definitions to produce the imine of formula XVI

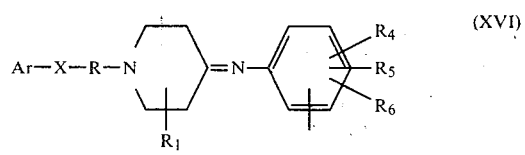     (XVI)

wherein the substituents Ar, X, R, $R_1$, $R_4$, $R_5$ and $R_6$ have the previously-given definitions which is further reacted with a reducing agent such as an alkali metal complex hydride, as exemplified above, to obtain the desired compound of formula V.

As examples of preferred arylamines of formula XV, may be cited 4-methoxyaniline, which leads to a 4-methoxyphenylamino derivative of formula V compounds; 3,4-methylenedioxyphenylamine, which gives rise to the formation of a 3,4-methylenedioxyphenylamino derivative compound of formula V; 3,4,5-trimethoxyphenylamine, which is used to obtain a 3,4,5-trimethoxyphenylamino compound of formula V; and, 2,6-dichloroaniline, which can be used to form a 2,6-dichlorophenylamino compound of formula V.

Another process for producing the compounds of formula I may also be utilized. It consists in reacting a 4-amino piperidine of formula II

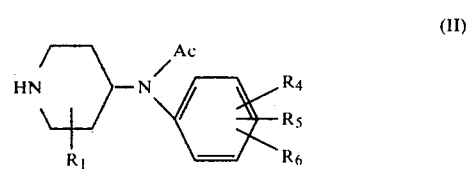     (II)

wherein the substituents $R_1$, Ac, $R_4$, $R_5$ and $R_6$ have the above-given definitions, with a bifunctional lower alkylene derivative of the formula IX

     (IX)

in which Y and R are defined as above-given to produce a 1-(4-amino piperidino) alkanol of the formula X

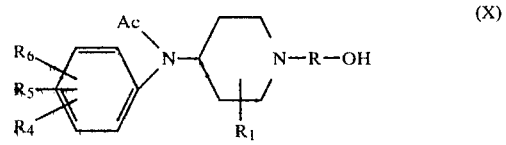     (X)

in which the substituents R, $R_1$, Ac, $R_4$, $R_5$ and $R_6$ have the previously-given meanings submits the latter to the action of a halogenating agent to produce the corresponding halide of the formula XI

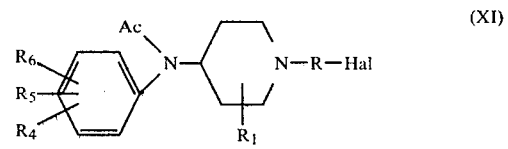     (XI)

in which Hal is a halogen atom and $R_1$, R, Ac, $R_4$, $R_5$ and $R_6$ are defined as above, and reacts the latter with an aryl derivative of the formula IV

     (IV)

in which Ar and X have the previously-given meanings and recovers the desired compound of formula I.

Preferably the halogenating agent is a halogenated derivative of an oxyacid such as phosphorus tribromide, phosphorus oxychloride, sulfuryl chloride, thionyl chloride; or an aryl sulphonyl halide such as p.toluene sulphonyl chloride or a metallic halide such as vanadium chloride.

The condensation of the halide of formula XI with the aryl derivative of formula IV is preferably performed in basic medium and namely in the presence of an alkaline reagent such as sodium hydroxide or potassium hydroxide.

The invention also extends to intermediate compounds useful for preparing the compounds of formula I the piperidino lower alkanols of the formula X

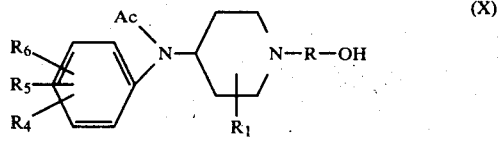

in which the substituents R, $R_1$, Ac, $R_4$, $R_5$ and $R_6$ are defined as previously indicated and the piperidino lower alkylene halides of the formula XI

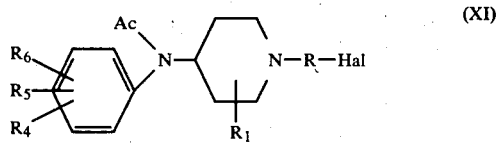

in which the substituents R, $R_1$, Ac, $R_4$, $R_5$ and $R_6$ have the previously-given meanings and Hal is a halogen.

The starting material of general formula III may be conveniently produced from a thiophenol of formula Ar—SH or from an arylamine of formula Ar—NHR' by reacting an epoxy lower alkane to produce an aryl lower alkanol of general formula VIII Ar—X—R—OH  (VIII)

which is further halogenated by means of a halogenating agent such as phosphorus tribromide, iodhydric acid or p.toluenesulphonyl chloride.

The 4-amino piperidines of general formula II or formula V are obtained according to the processes known from the literature and more precisely from the process disclosed in the German Pat. No. 1.470.357.

The following examples are merely intended to illustrate the invention. They do not limit it in any manner.

EXAMPLE I

1-[2-(thienyl-2-thio)-ethyl]-4-(N phenyl N-propionylamino) piperidine

Step A: 2-thienylthiol

In a three-neck flask, 100 ml tetrahydrofuran and 10.6 ml thiophene are added. The mixture is cooled to −40° C. then 59 ml of a 2.35 M solution of butyl lithium in n-hexane are added thereto in about 5 mn. After one hour of reaction while keeping the inner temperature at about −30° C., the mixture is cooled to −70° and 4.1 g sulphur are added. The mixture is kept aside for one and half hour. The reaction mixture becomes brownish. It is poured in a mixture of water and ice under constant stirring. The aqueous phase is decanted. The organic phase is extracted with few ml water. The aqueous solutions are united, cooled to about 0° and made acid by adding a 4 N solution of sulphuric acid. The aqueous solution is extracted three times with ether, the ethereous phases are separated, washed with water, dried on sodium sulphate, filtered and evaporated to dryness. The dry residue is further purified by fractionated distillation under reduced pressure—3.6 g thienyl-2-thiol are recovered. The pure compound boils at 60°–65° C. under 15 mmHg.

Thienyl-2-thiol is used as such for the next step of the synthesis.

Step B: 1[2-(thienyl-2-thio)-ethyl]-4-(N-phenyl N-propionylamino) piperidine

In a flask fitted with a mechanical stirring they are successively added 3.6 g thienyl-2-thiol, 3.6 g sodium hydroxide and 15 ml water. To the suspension 6 g of 1-(N-β-chloroethyl) 4-(N-phenyl N-propionylamino) piperidine (hydrochloride) previously dissolved in 25 ml water, are added. The whole mixture is heated to reflux for 3 hours. An oily precipitate appears which is extracted three times with ether at ambient temperature. The ethereous phases are united, washed with aqueous sodium carbonate then twice with water, dried on sodium sulphate, filtered and distilled off—6.7 g of an oily residue are recovered. The raw product is taken up in an aqueous solution of methane sulphonic acid. The insoluble matter is separated by extraction with ether and the aqueous phase is made alkaline by adding a 2 N sodium hydroxide solution. The alkalinized solution is extracted with ether, and the ethereous phase is decanted, dried and filtered. After evaporation to dryness, 5.4 g of pure compound are isolated.

For analytical purpose the product is further purified by recrystallizing it from petroleum ether then from cyclohexane 1-[2-(thienyl-2-thio)-ethyl]-4-(N-phenyl N-propionylamino) piperidine is obtained with a yield of 58%. This compound melts at 78°

| Analysis $C_{20}H_{26}N_2OS_2$ = 374.57 | | | | |
|---|---|---|---|---|
| | C | H | N | S % |
| Calculated | 64.13 | 7.00 | 7.48 | 17.12 |
| Found | 64.07 | 7.05 | 7.40 | 17.18 |

Using the same procedure but starting from 3,4-dimethoxy phenylthiol, 1-[2-(3,4-dimethoxy phenylthio)-ethyl]-4-(N-phenyl N-propionylamino) piperidine is obtained.

Starting from 4-dimethylamino phenylthiol, 1-[2-(4-dimethylaminophenylthio)-ethyl]-4-(N-phenyl N-propionylamino) piperidine is produced.

Starting from 3,4-methylene dioxy phenylthiol, 1-[2-(3,4-methylene dioxy phenylthio)-ethyl]-4-(N-phenyl N-propionylamino) piperidine is produced.

Starting from 2,5-dimethyl phenylthiol, 1-[2-(2,5 dimethyl phenylthio)-ethyl]-4-(N-phenyl N-propionylamino) piperidine is produced.

Starting from 2-ethoxy carbonyl phenylthiol, 1-[(2-ethoxy carbonyl phenylthio)-ethyl]-4-(N-phenyl N-propionylamino) piperidine is produced.

Starting from 2-methoxy phenylthiol, 1-[(2-methoxy phenylthio)-ethyl]-4-(N-phenyl N-propionylamino) piperidine is produced.

Starting from 2-methoxy 5-chloro phenylthiol, 1-[(2-methoxy 5-chloro phenylthio)-ethyl]-4-(N-phenyl N-propionylamino) piperidine is produced.

The starting material, 1-N(β-chloroethyl)-4-(N phenyl N-propionylamino) piperidine is obtained from 1-(β-hydroxyethyl) 4-(N-phenyl N-propionylamino)

piperidine by reaction of thionyl chloride; 1-(β-hydroxyethyl)-4-(N-phenyl N-propionylamino) piperidine is produced by reacting ethylene oxide with 4-(N-phenyl N-propionylamino) piperidine.

Additional compounds of this invention include:
1-[2-(p-methoxyphenylamino)ethyl]-4-(N-phenyl-N-propionylamino)piperidine, obtained from p-methoxyaniline and 1-(N-β-chloroethyl)-4-(N-phenyl-N-propionylamino)piperidine;
1-[2-(2-ethoxy-5-chlorophenylamino)ethyl]-4-(N-phenyl-N-propionylamino)piperidine, from 5-chloro-o-phenetidine;
1-[2-(2-methoxy-4-chlorophenylamino)ethyl]-4-(N-phenyl-N-propionylamino)piperidine, from 5-chloro-o-anisidine;
1-[2-(3,5-dichloro-4-ethoxyphenylamino)ethyl]-4-(N-phenyl-N-propionylamino)piperidine, from 3,5-dichloro-4-ethoxyaniline;
1-[2-(pentabromophenylamino)ethyl]-4-(N-phenyl-N-propionylamino)piperidine, from pentabromoaniline;
1-[2-(2,4,6-tribromophenylamino)ethyl]-4-(N-phenyl-N-propionylamino)piperidine, from 2,4,6-tribromoaniline;
1-[2-(2-methoxy-5-aminosulphonylphenylamino)ethyl]-4-(N-phenyl-N-propionylamino)piperidine, from 2-methoxy-5-aminosulphonylaniline;
1-[2-(2,4-dimethoxyphenylamino)ethyl]-4-(N-phenyl-N-propionylamino)piperidine, from 4-aminoresorcinol;
1-[2-(4-methylmercaptophenylamino)ethyl]-4-(N-phenyl-N-propionylamino)piperidine, from 4-methylmercaptoaniline, and the like.

EXAMPLE II

1-[2-(2,6-dimethyl phenylthio)-ethyl]-4-(N-phenyl N-propionylamino) piperidine

Step A: 2-(2,6-dimethyl phenylthio) 1-hydroxyethane 35 g. 2,6-dimethyl thiophenol are dissolved in a solution of 15.6 g sodium hydroxide in 210 ml water, under stirring and inert atmospher. After complete dissolution 34 g chloro ethanol are added portionwise thereto and the milky suspension is thereafter heated to reflux for one hour. The mixture reverts to room temperature and is extracted three times with ester to isolate the thus formed oily product. The ethereous solutions are washed with water, dried on sodium sulphate, filtered and evaporated off. 2-(2,6-dimethyl phenylthio) 1-hydroxy ethane is obtained with a yield of 95%. It is further used for the next step without any purification Step B: 2-(2,6-dimethyl phenylthio) 1-bromoethane 18.2 g of 2-(2,6-dimethyl phenylthio) 1-hydroxy ethane and 50 ml chloroform are added in a flask and when the mixture is perfectly clear, it is cooled to 0°. To the solution 14.3 g of phosphorous tribromide are added while keeping the temperature to about 0°. After completion of the addition, the inner temperature is let to revert at ambiant temperature then heated to reflux for one hour.

The reaction mixture is thereafter cooled and poured in a mixture of water and ice and the precipitate is extracted with a mixture of ether and chloroform. The organic solutions are separated, washed with a 5% solution of sodium carbonate, then with water, dried on sodium sulphate and evaporated to dryness. A dry residue, weighing 24.2 g is recovered and further purified by distillating it under reduced pressure—21.2 g of 2-(2,6-dimethyl phenylthio) 1-bromoethane are obtained. The yield amounts to 86%. This compound boils at 155° C. under 16 mmHg.

| Analysis $C_{10}H_{13}BrS$ = 245.18 | | | |
|---|---|---|---|
| | C | H | S | Br % |
| Calculated | 48.99 | 5.34 | 13.08 | 32.59 |
| Found | 49.58 | 5.33 | 13.22 | 32.35 |

Infrared Spectrum: compatible with the proposed structure lack of starting hydroxylated compound Step C: 1[2-(2,6-dimethyl phenylthio)-ethyl]-4-(N-phenyl N-propionylamino) piperidine 8.5 g of 2-(2,6-dimethyl phenylthio) 1-bromoethane obtained at step B are dissolved in 200 ml methyl isobutyl ketone. To this solution, 8.1 g of 4-(N-phenyl N-propionylamino) piperidine then 11.2 g anhydrous sodium carbonate and few mg potassium iodide are added and the whole mixture is heated to reflux for 2 hours. The precipitate is thereafter separated by filtration and the filtrate evaporated off. The dry residue, weighing 14.6 g is taken up in the minimal amount of ether to dissolve it. The ethereous solution is extracted with N aqueous solution of hydrochloric acid. The hydrochloride of 1-[2-(2,6-dimethyl phenylthio)-ethyl]-4-(N-phenyl N-propionylamino) precipitates and is separated by filtration. It is further taken up with water, then the aqueous suspension is made freely basic by adding a 2 N solution of sodium hydroxide.

The aqueous phase is extracted with ether three times, the ethereous solutions are separated, washed with water, dried and evaporated under vacuum.

9.4 g of free base are recovered. It crystallises from scratching with few drops of isopropyl ether. After further recrystallization from isopropyl ether, a first crop of 1-[2-(2,6-dimethyl phenylthio)-ethyl]-4-(N-phenyl N-propionylamino) piperidine weighing 6.6 g is obtained. This compound melts at 85°.

| Analysis: $C_{24}H_{32}OS$ = 396.58 | | | |
|---|---|---|---|
| | C | H | N | S % |
| Calculated | 72.69 | 8.13 | 7.07 | 8.09 |
| Found | 72.90 | 7.98 | 7.06 | 8.49 |

Infra-red spectrum: in accordance with the structure. Stretching at 1640 cm$^{-1}$ (tertiary amide)

The starting material, 2,6-dimethylthiophenol, is produced from o.xylidine by diazotation, decomposition of the diazonium salt in the presence of potassium ethyl xanthate and finally decomposing the xanthate thus formed, by addition of potash then acidifying with a strong acid 2,6-dimethylthiophenol boils at 94°–96° under 20 mmHg

| Analysis: $C_8H_{10}S$ = 138 | | |
|---|---|---|
| | C | H | S % |
| Calculated | 69.52 | 7.29 | 23.20 |
| Found | 69.80 | 7.49 | |

EXAMPLE III 1-(2-phenylthio-ethyl)-4-(N-phenyl N-propionylamino) piperidine

Using the process of example II and starting from benzenethiol, there are successively obtained:
(2-hydroxyethyl) thiophenol
(2-bromoethyl) thiophenol BP=132–136/13 mm

| Analysis: $C_8H_9BrS = 217.12$ | | | | |
|---|---|---|---|---|
| | C | H | S | Br % |
| Calculated | 44.26 | 4.18 | 14.76 | 36.80 |
| Found | 44.58 | 4.20 | 15.00 | 36.41 |

1-(2 phenylthio-ethyl)-4-(N-phenyl N-propionylamino) piperidine

Its hydrochloride melts at 183°. It is fairly soluble in water.

EXAMPLE IV

1-[2-(2,6-dichlorophenylamino)-ethyl]-4-(N-phenyl N-propionylamino) piperidine

Using the same procedure as in example II and starting from 2,6-dichloro aniline, there are successively obtained:
N-(2-hydroxyethyl) 2,6-dichloroaniline
N-(2-bromoethyl) 2,6-dichloroaniline
1-[2-(2,6-dichlorophenylamino)-ethyl]-4-(N-phenyl N-propionylamino) piperidine which melts at 82°–84° (from petroleum ether)

| Analysis: $C_{22}H_{27}Cl_2ON_3 = 420.38$ | | | | |
|---|---|---|---|---|
| | C | H | N | Cl % |
| Calculated | 62.85 | 6.47 | 9.99 | 16.86 |
| Found | 63.10 | 6.57 | 9.97 | 16.68 |

Infra-red spectrum = compatible with the proposed structure
stretchings at 3320cm$^{-1}$ (group —NH—)
stretchings at 1640cm$^{-1}$ (carbonyl of a tertiary amide)

EXAMPLE V

1-[2-(2,6-dimethyl phenylamino)-ethyl]-4-(N-phenyl N-propionylamino) piperidine

Using the procedure of example II but starting from o.xylidine, there are successively obtained:
N-(β-hydroxyethylamino) 2,6-dimethyl benzene, BP=105°–110°/0.15 mmHg
N-(β-bromoethylamino) 2,6-dimethyl benzene (hydrobromide) MP=240°–250° (sublim.)

| Analysis: $C_{10}H_{14}NBr,BrH = 309.06$ | | | | |
|---|---|---|---|---|
| | C | H | N | Br % |
| Calculated | 38.86 | 4.89 | 4.53 | 51.71 |
| Found | 38.98 | 5.17 | 4.64 | 51.60 |

1-[2-(2,6-dimethyl phenylamino)-ethyl]-4-(N phenyl N-propionylamino) piperidine

Its melts at 68°–70°. It is soluble in the stoichiometric amount of methane sulphonic acid giving rise to the methane sulphonate after evaporation of the solvent

| Analysis: $C_{24}H_{33}N_3O = 379.55$ | | | |
|---|---|---|---|
| | C | H | N % |
| Calculated | 75.94 | 8.76 | 11.07 |
| Found | 75.55 | 8.52 | 11.00 |

EXAMPLE VI

1-[2-(N-phenyl N-methylamino)-ethyl]-4-(N-phenyl N-propionylamino) piperidine

Using the same procedure as in example II but starting from N-methyl aniline, there are produced:
N(β-hydroxyethyl) N-methyl aniline
N(β-chloroethyl) N-methyl aniline
1-[2-(N-phenyl N-methylamino) ethyl]4-(N-phenyl N-propionylamino) piperidine
It melts at 88°–90° (from isopropyl ether)
The compound is soluble in an aqueous solution of methane sulphonic acid

| Analysis: $C_{23}H_{31}N_3O = 365.52$ | | | |
|---|---|---|---|
| | C | H | N % |
| Calculated | 75.57 | 8.54 | 11.49 |
| Found | 75.70 | 8.51 | 11.41 |

The same compound may be also be produced starting from 1-[(2-phenylamino)-ethyl]-4-(N-phenyl N-propionylamino) piperidine and performing the methylation by means of a mixture of formol and formic acid.

EXAMPLE VII

1-[2-(phenylamino-)ethyl]-4-(N-phenyl N-propionylamino) piperidine

Using the same procedure as in example II the following compounds have been obtained, starting from aniline:
(β-hydroxyethyl) aniline
(β-bromoethyl) aniline
1-[2-(phenylamino)-ethyl]-4-(N-phenyl N-propionylamino) piperidine.
This compound melts at 74°–76° C. It is soluble in hydrochloric acid and in methane sulphonic acid dissolved in a mixture of water and propyleneglycol

| Analysis: $C_{22}H_{29}N_3O = 351.49$ | | | |
|---|---|---|---|
| | C | H | N % |
| Calculated | 75.17 | 8.31 | 11.95 |
| Found | 75.06 | 8.50 | 11.94 |

EXAMPLE VIII

1-[2-(N-acetyl N-phenylamino)-ethyl]-4-(N-phenyl N-propionylamino) piperidine

By reaction of excess of acetic anhydride on 1-[2-(-phenylamino)-ethyl]-4-(N-phenyl N-propionylamino) piperidine, 1-[(N-phenyl N-acetylamino)-ethyl]-4-(N-phenyl N-propionylamino) piperidine is obtained. It melts at 146° (from cyclohexane). It is soluble in hydrochloric acid.
Infra-red spectrum:
absence of stretching corresponding to the group —NH— presence of a more intense carbonyl band at 1640 cm$^{-1}$

| Analysis: $C_{24}H_{31}N_3O_2$ = 393.53 | | | |
|---|---|---|---|
| | C | H | N% |
| Calculated | 73.25 | 7.95 | 10.67 |
| Found | 73.49 | 8.05 | 10.69 |

Using the same procedure but starting from 1-[2-(2,6-dimethyl phenylamino)-ethyl]-4-(N-phenyl N-propionylamino) piperidine and butyroyl chloride, 1-[2-(N-(2,6-dimethyl phenyl) N-butyrylamino)-ethyl]-4-(N-phenyl N-propionylamino) piperidine is produced.

Similarly using dipropyl acetyl chloride as the acylating agent, 1-[2-(N-(2,6-dimethyl phenyl) N-dipropylacetylamino-ethyl]-4-(N-phenyl N-propionylamino) piperidine is produced.

EXAMPLE IX

1-[2-(N-phenyl N-allylamino)-ethyl]-4-(N-phenyl N-propionylamino) piperidine

Using the same procedure as in example II and starting from aniline, the following compounds are produced:
N-allyl aniline
N-allyl N-(β-hydroxyethyl) aniline
N-allyl N-(β-bromoethyl) aniline
1-[2-(N-phenyl N-allylamino)-ethyl]-4-(N-phenyl N-propionylamino) piperidine.

The title compound may also be obtained starting from N-allyl aniline, by reaction with sodium in liquid ammonia, then reaction of the sodio derivative with 1-(β-chloroethyl)-4-(N-phenyl N-propionylamino) piperidine.

EXAMPLE X cis dl 1-[2-(2,6-dimethyl phenylamino)-ethyl]-3-methyl-4-(N-phenyl N-propionylamino) piperidine Reacting an excess of propionic anhydride with 2.7 g of cis dl 3-methyl-4-phenylamino piperidine, 2.6 g of cis dl 3-methyl-4-(N-phenyl N-propionylamino) piperidine are obtained. The latter is condensed with N-(β-bromoethylamino) 2,6-dimethyl benzene to produce cis dl 1-[2-(2,6-dimethyl phenylamino)-ethyl]-3-methyl-4-(N-phenyl N-propionylamino) piperidine.

EXAMPLE XI

Pharmacological study of the compounds according to the invention.

(a) acute toxicity of the compounds

The average lethal dosage of the compounds has been determined in batches of male mice (strain Swiss) weighing about 20 g. They receive either intraperitoneally the compound to be tested in suspension in an aqueous solvent or orally dissolved in an aqueous solution of arabic gum.

The animals are kept under survey for 8 days and the deaths, if any, are numbered for each batch. The average lethal dosage is graphically calculated according to the method described in Tainter and Miller.

Intraperitoneously the average lethal dosage ranges, depending on the compound, from 30 to 200 mg/kg.

Orally the average lethal dosage ranges from 250 to 1000 mg/kg.

(b) hypotensive activity

The compounds of general formula I have been administered to batches of normal dogs, previously anaesthetized with Nembutal, at increasing dosage ranging from 0.5 to 5 mg/kg. Depending on the tested compound the mean arterial pressure is decreased of 20 to 40% and the cardiac rhythm is reduced of 30 to 40%. The duration of both activities extends from 20 to 45 mn.

(c) search of a neurological effect

In the mice (strain CD) the first active dosage on the Central Nervous System is of 5 to 10 mg/kg intraperitoneously. At this dosage the only effect is a slight increase of the motility. At a dosage of 25 mg/kg intraperitoneously the neurological effects are still very limited (slight increase in the muscular tone, decrease of the sensibility and the reflexes). In the cat the mere effects are a decrease in the reflexes and in the muscular strenghth.

Moreover by oral administration the neurological effects are still more attenuated. The first orally-active dosage in the mice is about 50 mg/kg and induces a slight increase of the muscular tone.

At a dosage of 100 mg/kg orally, the respiration is slightly depressed, and mydriasis appeared. Higher dosages cause deaths.

It may be stated that the compounds of general formula I do not induce any significant effect on the Central Nervous System. They are neither neuro-depressant nor depressant of the respiratory center to a significative degree.

What we claim is:
1. Aryl alkyl piperidines of the formula I

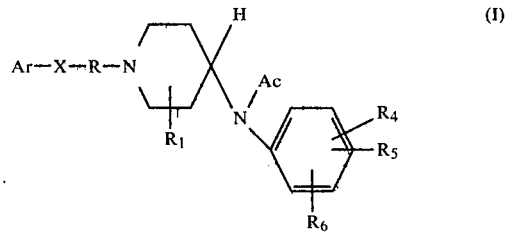

in which
$R_1$ is a hydrogen or a lower alkyl radical,
R is an alkylene chain having from 2 to 4 carbon atoms which may be substituted with one or more lower alkyl radicals,
X is a grouping

in which $R_2$ is hydrogen, a lower alkyl carbonyl residue, a lower alkenyl radical or a lower alkyl radical;
Ac is an acyl residue from an alkyl carboxylic acid having up to 10 carbon atoms;
$R_4$, $R_5$ and $R_6$ which are the same or different represent a hydrogen, a halogen, a lower alkyl radical, a lower alkoxy or a lower alkylene dioxy;
and Ar is an unsubstituted phenyl or substituted phenyl radical of the formula

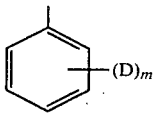

wherein D is a halogen, a lower alkyl radical, a lower alkenyl radical, a lower alkoxy, a lower alkenyloxy, a lower alkynyloxy, a lower alkylthio, a hydroxy carbonyl, a lower alkoxy carbonyl, a nitro group, an amino, a lower alkyl amino, a di-lower alkyl amino, a lower acylamino, a sulphonamido, a lower alkyl amino sulphonyl, a dilower alkyl amino sulphonyl, a lower alkyl sulphonyl, an amino carbonyl, a cyano, a trifluoromethyl or a lower alkylene dioxy and m is O or an integer from 1 to 5, inclusive.

2. A compound according to claim 1 having the general formula $I_C$

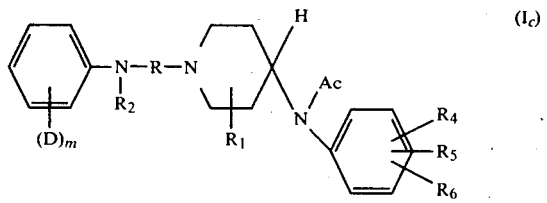

in which the substituents D, R, $R_1$, $R_4$, $R_5$, $R_6$ and m are defined as above-indicated and $R_2$ is a hydrogen, a methyl, an ethyl, an allyl or an acetyl group.

3. The acid addition salts of a compound of claim 1.

4. The optically-active isomers or diastereo isomers of a compound of claim 1.

5. 1-[2-(phenylamino)ethyl]-4-(N-phenyl-N-propionylamino)piperidine, according to claim 1.

6. 1-[2-(N-phenyl-N-methylamino)ethyl]-4-(N-phenyl-N-propionylamino)piperidine, according to claim 1.

7. 1-[2-(2,6-dichlorophenylamino)ethyl]-4-(N-phenyl-N-propionylamino)piperidine, according to claim 1.

8. 1-[2-(N-phenyl-N-acetylamino)ethyl]-4-(N-phenyl-N-propionylamino)piperidine, according to claim 1.

9. 1-[2-(2,6-dimethylphenylamino)ethyl]-4-(N-phenyl-N-propionylamino)piperidine, according to claim 1.

10. 1-[2-(N-phenyl-N-allylamino)ethyl]-4-(N-phenyl-N-propionylamino)piperidine, according to claim 1.

11. 1[2-(2-methoxy phenylamino)ethyl]4-(N-phenyl N-propionylamino) piperidine, according to claim 1.

12. 1-[2-(2-ethoxy 5-chlorophenylamino)ethyl]4-(N-phenyl N-propionylamino) piperidine, according to claim 1.

13. 1-[(2-(2-methoxy 4-chlorophenylamino)ethyl]4-(N-phenyl N-propionylamino) piperidine, according to claim 1.

14. 1-[2-(2-methoxy 5-chlorophenylamino)ethyl]4-(N-phenyl N-propionylamino) piperidine, according to claim 1.

15. 1-[2-(3,5-dichloro 4-ethoxyphenylamino)ethyl]4-(N-phenyl N-propionylamino) piperidine, according to claim 1.

16. 1-[2-(pentabromophenyl)amino ethyl]4-(N-phenyl N-propionylamino) piperidine, according to claim 1.

17. 1-[2-(2,4,6-tribromophenylamino)ethyl]4-(N-phenyl N-propionylamino) piperidine, according to claim 1.

18. 1-[2-(2-methoxy 5-aminosulphonylphenylamino)ethyl]4-(N-phenyl N-propionylamino) piperidine, according to claim 1.

19. 1-[2-(2,4-dimethoxy phenylamino)ethyl]4-(N-phenyl N-propionylamino) piperidine, according to claim 1.

20. 1-[2-(4-methylmercaptophenylamino)ethyl]4-(N-phenyl N-propionylamino), according to claim 1.

21. A pharmaceutical composition useful in treatment of hyperetension incorporating as active ingredient at least one compound of claim 1 or a salt thereof with a mineral or organic acid, in admixture with an inert non-toxic, therapeutically-acceptable carrier.

22. A pharmaceutical composition according to claim 21, in which the inert carrier is intended for the oral, parenteral, sublingual or rectal route of administration.

23. A pharmaceutical composition according to claim 21, in which the amount of active ingredient ranges from 1 to 250 mg per unit dosage.

24. A method for treating hypertension in a human or domestic animal patient suffering from hypertension, which comprises administering to said patient an antihypertensive amount of a compound of claim 1.

25. The method of claim 24, in which he antihypertensive amount of a compound of claim 1 ranges from 0.03 to 15 mg/kg per day.

* * * * *